US007015014B2

(12) United States Patent
Schaap et al.

(10) Patent No.: US 7,015,014 B2
(45) Date of Patent: Mar. 21, 2006

(54) ISOLATION OF CAROTENOID CRYSTALS

(75) Inventors: Albert Schaap, Barendrecht (NL);
Mieke Sibeijn, Amersfoort (NL);
Johannes Hendrik Wolf, Rijswijk (NL)

(73) Assignee: DSM IP Assets B.V., Te Heerlen (NL)

( * ) Notice: Subject to any disclaimer, the term of this patent is extended or adjusted under 35 U.S.C. 154(b) by 246 days.

(21) Appl. No.: 10/182,328

(22) PCT Filed: Jan. 29, 2001

(86) PCT No.: PCT/EP01/00975

§ 371 (c)(1),
(2), (4) Date: Jul. 29, 2002

(87) PCT Pub. No.: WO01/55100

PCT Pub. Date: Aug. 2, 2001

(65) Prior Publication Data

US 2003/0139480 A1    Jul. 24, 2003

(30) Foreign Application Priority Data

Jan. 27, 2000 (EP) ................................ 00200308

(51) Int. Cl.
*C12P 23/00* (2006.01)
*C12N 1/14* (2006.01)
*C12N 1/16* (2006.01)
*C07C 403/00* (2006.01)

(52) U.S. Cl. ..................... 435/67; 435/171; 435/254.1; 554/14; 554/19; 554/20; 568/830; 585/351; 585/836

(58) Field of Classification Search ................. 435/67, 435/171, 254.1; 585/351, 836; 554/14, 554/19, 20; 568/830
See application file for complete search history.

(56) References Cited

U.S. PATENT DOCUMENTS

| 3,268,606 | A | | 8/1966 | Jaeger ........................ 260/666 |
| 4,439,629 | A | | 3/1984 | Rüegg ........................ 585/803 |
| 5,310,554 | A | * | 5/1994 | Haigh ........................ 424/439 |
| 5,648,564 | A | * | 7/1997 | Ausich et al. ............... 568/834 |
| 6,262,284 | B1 | * | 7/2001 | Khachik ....................... 554/14 |
| 6,812,001 | B1 | * | 11/2004 | Sibeijn et al. ................. 435/67 |

FOREIGN PATENT DOCUMENTS

| CN | 1242417 | 1/2000 |
| WO | WO 97/23436 | 7/1997 |
| WO | WO 97/31894 | 9/1997 |
| WO | WO 98/03480 | 1/1998 |
| WO | WO 98/43620 | 10/1998 |
| WO | WO 98/50574 | 11/1998 |
| WO | WO 99/20587 | 4/1999 |

* cited by examiner

*Primary Examiner*—Herbert J. Lilling
(74) *Attorney, Agent, or Firm*—Morrison & Foerster LLP

(57) ABSTRACT

The present invention relates to a crystalline carotenoid compound, such as β-carotene, with a purity of at least 95% and with substantially no solvent enclosed in the crystal lattice. The present invention further describes a process to prepare such a highly pure crystalline carotenoid compound from microbial biomass, without the use of a solvent extraction and/or an anti-solvent crystallization process.

17 Claims, No Drawings

ISOLATION OF CAROTENOID CRYSTALS

FIELD OF THE INVENTION

The present invention relates to a crystalline carotenoid compound with a purity of ≧95% without any substantial amount of organic solvent enclosed within the crystal lattices of the crystalline carotenoid and a process to prepare the same.

BACKGROUND OF THE INVENTION

Carotenoids are the most numerous and widespread group of pigments to be found in nature. Some particular examples of carotenoid compounds are: β-carotene, β-apo-4'-carotenal, β-apo-8'-carotenal, β-apo-12'-carotenal, β-apo-8'-carotenic acid, astaxanthin, canthaxanthin, zeaxanthin, cryptoxanthin, citranaxanthin, lutein, lycopene, torularodinaldehyde, torularodin-ethylester, neurosporaxanthinethylester, zeta-carotene and dehydroplectaniaxanthin. Moreover, the carotenoid is known as one of the pigments that are widely used for colouring of food, cosmetics, medicines, and the like.

Carotenoid crystals are usually produced by a conventional chemical process. However, now-a-days there is a substantial demand for products derived from natural sources. When derived from a natural source, the carotenoid mostly is in the form of an oily extract (palm oil, algae oil). Although it is also possible to obtain a crystalline carotenoid, for instance, carotene, from natural sources, such as vegetables (for example carrots) or microorganisms (for example algae (*Dunaliella*) or fungi (*Blakeslea*)), the currently available processes to obtain relatively pure crystals from said natural sources have important disadvantages.

Isolation of crystalline carotenoid, such as β-carotene, from natural sources comprises for instance extraction of the β-carotene from said source, such as mentioned in international patent application WO 9803480, and additional purification steps. The extraction is carried out with various organic solvents, such as acetone, ethyl acetate, butyl acetate, hexane, dichloromethane or hexane, vegetable oils, or supercritical fluids, such as propane, ethylene or carbon dioxide. To obtain a relatively pure β-carotene preparation, a further purification of the extract is necessary. Several purification processes have been described, among which chromatography, adsorption/desorption processes and crystallization or precipitation.

Carotenoid crystals which are crystallized from the extract obtained after solvent extraction of a suitable natural source, for example by evaporation of the solvent, have an odor peculiar to the starting material and typically contain some impurities, for instance the solvent itself and impurities originating from the extraction step. In such cases recrystallizations are required, for instance as described in U.S. Pat. No. 3,268,606 and U.S. Pat. No. 4,439,629. The main drawback of recrystallization is that a large amount of solvent is required to solubilize the carotene. In addition, to recrystallize the carotene with a sufficiently high yield, large amounts of anti-solvent (precipitating solvent) are necessary as well. Thus, these processes have the disadvantage that large amounts of solvents are required and a considerable loss of carotene can easily occur. Moreover, solvent will be enclosed within the crystal lattices of the crystalline carotenoid.

In international patent application WO 9850574, a process for the isolation of a crystalline carotenoid compound from microbial biomass has been described which comprises the steps of disrupting the microbial cell walls and separating cellular debris from the carotenoid containing residue, including a wash of the microbial biomass. The disrupted cell mass or the carotenoid containing residue is treated with a solvent suitable to remove lipid and suspending the obtained carotenoid crystals in water to float the crystals. Thereafter, the crystalline product is separated and, optionally, further purified. In the international patent applications WO 9843620, WO 9723436 and WO 9731894, a process for the preparation of carotenoid compound from oleoresins has been described, the process comprising a treatment with an alkaline reagent in an organic medium and then addition of an anti-solvent to obtain the crystalline carotenoid compound. The main disadvantage of both the dissolution of the disrupted cell mass in a solvent and the addition of an anti-solvent is the inclusion of solvent into the carotenoid crystals.

Surprisingly, we have found that very pure carotenoid crystals substantially free of solvent in the crystal lattice can efficiently be isolated from a crystalline suspension from a microbial source without the use of extraction/anti-solvent processes, yielding carotenoid crystals with a purity of at least 95%.

DETAILED DESCRIPTION OF THE INVENTION

The present invention discloses a crystalline carotenoid with a purity of ≧95%, preferably ≧96%, more preferably ≧97%, even more preferably ≧98%, most preferably ≧99%, which has substantially no solvent in the crystal lattice. By "substantially no solvent" is meant an amount of solvent of lower than 0.5% (w/w), preferably lower than 0.2% (w/w), more preferably lower than 0.1% (w/w), most preferably lower than 0.05% (w/w).

Furthermore, an efficient and robust process for the isolation of said carotenoid compound, preferably from microbial cells, is described. According to the process of the present invention, the carotenoid crystals are purified from microbial cells by removing all impurities present in a crystalline carotenoid suspension without enclosing solvent in the crystal lattice.

The process of the invention comprises the following steps:
(a) disruption of carotenoid-containing cells, preferably from a microbial source, and separation of an oily crystalline carotenoid suspension,
(b) treatment of the oily crystalline carotenoid suspension with alkali at a pH of 9–12 and at a temperature of 10–95° C., preferably 30–85° C., most preferably 50–75° C., optionally in the presence of a lower alcohol,
(c) optional addition of a salt to the alkali-treated crystalline carotenoid suspension,
(d) optional separation of the crystalline carotenoid suspension from the liquid phase,
(e) optionally washing the crystalline carotenoid suspension with a salt containing aqueous solution,
(f) washing the crystalline carotenoid suspension in a first washing procedure with a lower alcohol, wherein the order of performance of steps (b)–(e) and (f is arbitrary,
(g) washing the crude carotenoid crystals resulting from the (a)–(f) process steps in a second washing procedure with water or with a mixture of a lower alcohol and water,
(h) washing the crystals with a fresh solvent, and
(i) drying the crystals.

Carotenoid-containing microbial cells may be obtained from any suitable fermentation process of a carotenoidproducing microorganism of choice. The carotenoid-containing microorganism may be a bacterium, a fungus, an alga or a yeast. Preferably, it is a fungus of the order *Mucorales*, preferably *Blakeslea trispora*, an alga of the genus *Dunaliella*, or a yeast of the genus *Phaffia*, preferably *Phaffia rhodozyma*.

The resulting fermentation broth comprising microbial cells and fermentation fluid may be used directly for the isolation of carotenoid crystals. Alternatively, prior to carrying out the process of the invention, microbial cells may be separated from the fermentation fluid by any suitable method, such as filtration or centrifugation.

The carotenoid-containing microbial cells are opened by disrupting the cell walls by means of mechanical, chemical and/or enzymatic treatment. For instance, the cells may be subjected to homogenization, sonication, autolysis, osmolysis and/or plasmolysis, optionally with addition of suitable agents such as detergents, acids, bases, enzymes, autolysis-enhancing substances, osmolysing agents such as salts, and/or plasmolysing agents. In this way, an oily crystalline carotenoid suspension is released from the cells, whereupon the oily crystalline carotenoid suspension is separated from the cell debris, preferably by means of centrifugation.

The oily crystalline carotenoid suspension thus obtained is then further purified. Before applying the next purification step, the oily crystalline carotenoid suspension may be washed one or more times with water.

The next purification step consists of a treatment of the oily crystalline carotenoid suspension with alkali. The alkali treatment comprises the addition of an alkaline aqueous solution having a pH between 9 and 12 to the oily carotenoid suspension and the subsequent incubation, preferably under stirring, for an appropriate time period at a temperature between 10–95° C., preferably between 30–85° C., more preferably between 50–75° C. The ratio of alkaline solution to oily carotenoid suspension conveniently may vary from about 5:1 to about 1:1 (w/w). The duration of the alkali treatment typically will depend on the applied pH and temperature, in the sense that the lower the pH and temperature applied during treatment, the longer the treatment should be. For instance, the alkali treatment may be performed during 2 hours at pH 12 and a temperature of 75° C. or during 8 hours at pH 10 and a temperature of 50° C. Optionally, the alkali treatment may be carried out in the presence of a lower alcohol.

After alkali treatment, a water soluble salt, such as sodium chloride, may optionally be added to the alkali-treated crystalline carotenoid suspension. The crystalline carotenoid suspension may then be separated from the liquid phase and may optionally be washed with a salt containing aqueous solution. The separation of the crystalline carotenoid suspension may be carried out by any method known in the art, such as filtration, centrifugation or cooling.

The crystalline carotenoid suspension is then subjected to a first washing procedure comprising washing the suspension with a lower alcohol, yielding crude carotenoid crystals. This first washing procedure may be repeated one or more times.

Typically, a washing step performed according to the invention includes stirring the (oily) crystalline carotenoid suspension or the (crude) carotenoid crystals with the washing liquid and subsequently separating the (oily) crystalline carotenoid suspension or the crystals from the liquid phase.

In one embodiment of the invention, the crude carotenoid crystals are obtained by another order of the previous steps.

The oily crystalline carotenoid suspension obtained after separation of the crystals from the disrupted cells is firstly washed one or more times with a lower alcohol, followed by the alkali treatment as described before. The alkali treatment optionally is done in the presence of a lower alcohol. Alternatively, the first washing(s) with a lower alcohol are followed by washing the crystalline carotenoid suspension one or more times with alkaline water with a pH between 9 and 12, optionally in the presence of a lower alcohol and optionally at an elevated temperature.

Subsequently, the crystalline carotenoid suspension is separated from the liquid phase to yield crude carotenoid crystals.

Preferably, the process steps (a)–(f) as described above are performed in the order (a), (b), (c), (d), (e), (f).

Throughout the present invention, a lower alcohol is defined as a ($C_{1-6}$) alcohol, for instance methanol, ethanol, 1-propanol, 2-propanol and 1-butanol. The lower alcohol as used in the present invention may be a single alcohol or may be a mixture of two or more alcohols. Preferably, the lower alcohol is ethanol, 1-butanol or a mixture of 1-butanol and ethanol.

The crude carotenoid crystals are further purified by applying a second washing procedure comprising washing the crystals one or more times with water or with a mixture of a lower alcohol and water. The pH of the washing solution preferably has a value between 1 and 5, more preferably between 2 and 4. The water may be acidified with any suitable acid, such as sulphuric acid or hydrochloric acid or with an acidic buffer solution, such as a borate/hydrochloric acid or a citrate/hydrochloric acid buffer. The ratio of lower alcohol to water in the lower alcohol/water mixture preferably is between 5:1 and 1:5, more preferably between 1:1 and 1:2.

The crystals are subsequently separated from the liquid phase by any suitable method, such as filtration or centrifugation.

Hereafter, the crystals are washed one or more times with a fresh solvent. The fresh solvent is a lower alcohol, preferably ethanol, or an acetate ester of a lower alcohol, preferably ethyl acetate. More preferably, the fresh solvent is a food-grade solvent.

In a preferred embodiment of the invention, the lower alcohol used in the first two washing procedures of the crystalline carotenoid suspension and the fresh solvent used in the final washing step of the crystals are the same solvent.

In a final step of the process of the invention, the crystals are dried.

The process of the present invention results in crystals with a purity of at least 95% according to the analytical method as described in Food Chemical Codex (FCC), page 90, Edition IV (1996), National Academy Press, Washington D.C.

An important advantage of the present invention as compared to conventional extraction/crystallisation processes for the isolation of a crystalline carotenoid is that the use of organic solvent for the extraction of the carotenoid is avoided. As a consequence, substantially no solvent is incorporated in the crystal lattice of the resulting carotenoid compound.

In another aspect of the invention, the process of the present invention is used to increase the carotenoid content of any crude crystalline carotenoid composition, preferably of any crude crystalline carotenoid suspension.

β-Carotene and astaxanthin are the preferred carotenoid compounds of the present invention.

EXAMPLE 1

Preparation of β-carotene Crystals from the Crystalline β-carotene Suspension, Obtained from a Homogenized Fermentation Broth of *Blakeslea trispora*

(I). A fermentation broth of *Blakeslea trispora*, containing 0.9 g/l of β-carotene was homogenised once by means of a homogenizer (APV Gaulin) at 600 bar. Subsequently, the homogenised broth was centrifuged by means of a disc centrifuge. The top-layer containing the β-carotene crystals was recovered from the centrifuge. This top-layer was used as the starting material for various examples.

(II). 3000 ml of water were added to 2200 g of this β-carotene containing top-layer and subsequently the mixture was incubated during two hours at pH 12 (pH adjusted with 8 N NaOH) at 75° C. The reaction mixture was cooled to room temperature and 350 g of sodium chloride were added. The resulting mixture was centrifuged during five minutes at 5000 rpm. The crystalline β-carotene, suspension, thus obtained, was washed once with a buffer of pH 7 to which 50 g/l sodium chloride was added.

After centrifugation, the β-carotene suspension was washed four times with 2.5 volumes (about 5000 ml) of fresh 1-butanol. The resulting crystals recovered after centrifugation were washed three times with a mixture of 1-butanol and a buffer of pH 2 (citrate/hydrochloric acid) with a ratio of buffer to butanol of 2 to 1.

Finally, the β-carotene-enriched interface was washed twice with 2500 ml of 96% ethanol. The wet crystals, obtained after centrifugation were dried overnight under vacuum at 42° C.

The resulting crystals were analyzed according to the FCC method as described in the Food Chemical Codex, Edition IV (1996), National Academy Press, Washington D.C., page 90 with the following results:

FCC-specification isolated crystals

|  | FCC-specification | isolated crystals |
| --- | --- | --- |
| Assay: | >96%, <101% | 97.3% |
| Identification A: | 1.14–1.18 | 1.16 |
| Identification B: | >15 | 17.4 |
| Ash content: | <0.2% | 0.072% |

EXAMPLE 2

Preparation of Crystalline β-carotene from the Top-layer Containing β-carotene Crystals by Washing the Crystalline Product with a Mixture of 1-butanol, Ethanol and Water 1000 ml of water were added to 250 g of β-carotene suspension as recovered in Example 1(1) and incubated during two hours at pH 12 at 75° C. After cooling to room temperature 50 g of sodium chloride were added to the reaction mixture and the resulting mixture was centrifuged during five minutes at 5000 rpm.

The β-carotene suspension, thus obtained, was washed with a buffer of pH 7 to which 50 g/l sodium chloride was added. After centrifugation the suspension was washed with 2.5 volumes (=500 ml) of fresh 1-butanol. This step was repeated three times.

After washing with 1-butanol the pellet was washed three times with 250 ml of a mixture of 1-butanol, ethanol and water in the ratio of 2:3:1. Finally, the β-carotene-enriched pellet was washed twice with 50 ml of 96% ethanol. The resulting pellet after centrifugation was dried overnight under vacuum at 40° C. The purity of the obtained β-carotene crystals determined by the FCC method was 98% and the amount of solvent in the crystals was 870 ppm.

EXAMPLE 3

Preparation of Crystalline β-carotene from the Crystalline β-carotene Suspension by Washing the Suspension First with 1-butanol, Followed by Washing with 1-butanol and a Buffer of pH 10

250 g of the top-layer as recovered in Example 1(I) were washed with 2.5 volumes (=500 ml) of fresh 1-butanol. This step was repeated three times.

After washing with 1-butanol, the crystalline β-carotene suspension was suspended in a 250 ml of a mixture of 1-butanol and a buffer of pH 10 at room temperature. After centrifugation, the carotene suspension was washed twice with a mixture of 1-butanol and a buffer of pH 10. Finally, the β-carotene-enriched suspension was washed twice with 50 ml of 96% ethanol at a temperature of 50° C. for 30 minutes. The resulting crystals after centrifugation were dried overnight under vacuum at 40° C. The purity of the β-carotene crystals determined by the FCC method was 96%.

EXAMPLE 4

Isolation of Crystalline (β-carotene from a Suspension Containing β-carotene Crystals by Performing Repeatedly Washing with 1-butanol and Water Five different fermentation broths of *Blakeslea trispora* with an average β-carotene content of 1 g/l were homogenized once at 900 bar. The homogenized mixture of various broths was centrifuged, resulting in about 600 ml of the top-layer containing the (β-carotene crystals. The top-layer was washed three times with about 600 ml of demineralised water.

Subsequently 900 ml of water were added to 50 g of the recovered β-carotene suspension. The pH was adjusted to 12 with 8 N sodium hydroxide. After two hours of incubation at this pH and 75° C., the reaction mixture was cooled to room temperature.

250 ml of 1-butanol were added to 500 ml of the reaction mixture. After stirring for 5 minutes, the 1-butanol layer was decanted, and 250 ml of fresh 1-butanol were added. After a further stirring for 5 minutes, the mixture was centrifuged. The β-carotene crystals containing interface was separated, and suspended in a mixture of 20 ml of water and 15 ml of 1-butanol, stirred for 5 minutes and the interfacial layer containing the β-carotene crystals was separated by centrifugation. This step was repeated 5 times. Hereafter the β-carotene crystals were washed with 40 ml of ethanol (96%) and dried during 16 hr at 35° C. under vacuum. The purity of the obtained crystals was 97% according to the FCC method and the concentration of solvent was 340 ppm.

The invention claimed is:

1. A process for the preparation of a crystalline carotenoid compound with purity of ≧95% and that has substantially no solvent in its crystal lattice, comprising the steps of:
   (a) disrupting carotenoid-containing cells and separating an oily crystalline carotenoid suspension therefrom wherein no organic solvent is employed in said separation,
   (b) treating the oily crystalline carotenoid suspension with alkali at a pH of 9–12 and at a temperature of 10–95° C., optionally in the presence of a lower alcohol,
   (c) optionally adding a salt to the alkali-treated crystalline carotenoid suspension of step (b),
   (d) optionally separating the crystalline carotenoid suspension of step (b) from the liquid phase,
   (e) optionally washing the crystalline carotenoid suspension of step (b) with a salt containing aqueous solution,
   (f) washing the crystalline carotenoid suspension in a first washing procedure with a lower alcohol, wherein the order of performance of steps (b)–(e) and (f) is arbitrary,
   (g) washing the crude carotenoid crystals resulting from the (a)–(f) process steps in a second washing procedure with water or with a mixture of a lower alcohol and water,
   (h) washing the crystals with a fresh solvent, and
   (i) drying the crystals.

2. A process according to claim 1, wherein the steps (a)–(f) are performed in the order (a), (b), (c), (d), (e), (f).

3. A process according to claim 1, wherein the steps (a)–(f) are performed in the order (a), (f), (b), (c), (d), (e).

4. A process according to claim 1, wherein step (g) is performed at a pH between 1 and 5.

5. A process according to claim 1, wherein the lower alcohol is selected from the group consisting of ($C_{1-6}$) alcohols.

6. A process according to claim 1, wherein the fresh solvent used for washing the crystals in step (h) is ethanol or ethyl acetate.

7. A process according to claim 1, wherein the lower alcohol used in steps (a)–(g) and the fresh solvent used in step (h) are the same solvent.

8. A process according to claim 1, wherein the cells are of a bacterium, a fungus, an alga or a yeast.

9. A process according to claim 8, wherein the fungus belongs to the order Mucorales.

10. A process according to claim 9, wherein the fungus is *Blakeslea trispora*.

11. A process according to claim 8, wherein the yeast belongs to the genus *Phaffia*.

12. A process according to claim 1, wherein the carotenoid compound is β-carotene.

13. A process according to claim 1, wherein the carotenoid compound is astaxanthin.

14. A method for increasing the carotenoid content of a crystalline carotenoid composition by applying the process steps (b)–(i) of claim 1.

15. The process of claim 1 wherein the temperature in step (b) is 30–85° C.

16. The process of claim 15 wherein said temperature is 50–75° C.

17. The process of claim 5 wherein said alcohols are ethanol or 1-butanol.

* * * * *